(12) United States Patent
Ban et al.

(10) Patent No.: US 12,268,215 B2
(45) Date of Patent: Apr. 8, 2025

(54) BREAD COMPRISING SACCHARIFIED RICE SOLUTION AND METHOD FOR PREPARING SAME

(71) Applicant: SPC CO., LTD., Seongnam-si (KR)

(72) Inventors: Young Ju Ban, Seoul (KR); Gyeong Min Lee, Suwon-si (KR); Eun Hui Cho, Seoul (KR); Sang Min Shim, Anyang-si (KR); Jin Ho Seo, Seoul (KR)

(73) Assignee: SPC CO., LTD., Seongnam-si (KR)

( * ) Notice: Subject to any disclaimer, the term of this patent is extended or adjusted under 35 U.S.C. 154(b) by 334 days.

(21) Appl. No.: 17/802,323

(22) PCT Filed: Oct. 15, 2021

(86) PCT No.: PCT/KR2021/014352
§ 371 (c)(1),
(2) Date: Aug. 25, 2022

(87) PCT Pub. No.: WO2022/131508
PCT Pub. Date: Jun. 23, 2022

(65) Prior Publication Data
US 2023/0093128 A1 Mar. 23, 2023

(30) Foreign Application Priority Data
Dec. 16, 2020 (KR) ........................ 10-2020-0176742

(51) Int. Cl.
*A21D 10/00* (2006.01)
*A21D 2/18* (2006.01)
(Continued)

(52) U.S. Cl.
CPC ........... *A21D 10/002* (2013.01); *A21D 2/181* (2013.01); *A21D 8/042* (2013.01); *A21D 8/047* (2013.01);
(Continued)

(58) Field of Classification Search
CPC ..... A21D 8/047; A21D 13/047; A21D 10/002
See application file for complete search history.

(56) References Cited

FOREIGN PATENT DOCUMENTS

| CN | 100409753 C | 8/2008 |
|---|---|---|
| CN | 110800785 A | 2/2020 |

(Continued)

OTHER PUBLICATIONS

Machine translation of JP2013-153663 to Hata, publication date: Aug. 15, 2013. pp. 1-11. (Year: 2013).*

(Continued)

*Primary Examiner* — Jenna A Watts
(74) *Attorney, Agent, or Firm* — Sughrue Mion, PLLC

(57) ABSTRACT

The present invention relates to a bread comprising a saccharified rice solution and a method for preparing same and, more specifically, to a bread comprising a saccharified rice solution prepared by using *Aspergillus oryzae* koji, *Aspergillus kawachii* koji, and lees and a method for preparing same. According to the present invention, a saccharified rice solution prepared by using *Aspergillus oryzae* koji, *Aspergillus kawachii* koji, and lees is developed, and thus, as compared with an existing saccharified rice solution prepared by using *Aspergillus oryzae* koji or *Aspergillus kawachii* koji, sweetness may be reduced, and the amounts of glutamic acid and aspartic acid may be increased, thus giving further enhanced savory taste. Furthermore, various and rich flavors (aroma) may be enhanced. In addition, by addition of the saccharified rice solution of the present invention, a bread having savory taste and various and rich flavors (aroma) may be prepared.

6 Claims, 2 Drawing Sheets

(51) Int. Cl.
*A21D 8/04* (2006.01)
*A21D 8/06* (2006.01)
*A21D 13/047* (2017.01)
*C12N 1/18* (2006.01)
*C12R 1/69* (2006.01)

(52) U.S. Cl.
CPC .............. *A21D 8/06* (2013.01); *A21D 13/047* (2017.01); *C12N 1/18* (2013.01); *C12R 2001/69* (2021.05)

(56) References Cited

FOREIGN PATENT DOCUMENTS

| JP | 3701959 B1 | 10/2005 |
|----|------------|---------|
| JP | 2006-042679 A | 2/2006 |
| JP | 2013-102701 A | 5/2013 |
| JP | 2013-153663 A | 8/2013 |
| KR | 10-0803335 B1 | 2/2008 |
| KR | 10-1057598 B1 | 8/2011 |
| KR | 10-2012-0139155 A | 12/2012 |
| KR | 10-1399639 B1 | 5/2014 |
| KR | 10-1417288 B1 | 7/2014 |
| KR | 10-2014-0106306 A | 9/2014 |
| KR | 10-2015-0094016 A | 8/2015 |
| KR | 10-1750154 B1 | 6/2017 |
| KR | 10-1896372 B1 | 9/2018 |
| KR | 10-1926741 B1 | 12/2018 |
| KR | 10-2251300 B1 | 5/2021 |

OTHER PUBLICATIONS

Machine translation of KR2017-0121028 to Park, publication date Nov. 1, 2017. pp. 1-5. (Year: 2017).*
Ma, et al. "Modulation of fatty acid composition of Aspergillus oryzae in response to ethanol stress". Available online as of Jun. 1, 2019, in Microorganisms, 2019, 7, 158. pp. 1-12. (Year: 2019).*
Chinese Office Action dated Oct. 18, 2023 for counterpart Chinese patent application No. 2021800150897.
Yoon-Hee Choi et al., "Quality Changes of Steamed Rice Bread with Addition of Active Gluten and Rice Nuruk", Korean J. Food & Nutr., 2012, pp. 253-258, vol. 25, No. 2.
Korean Office Action for 10-2020-0176742 dated Feb. 18, 2021.
International Search Report for PCT/KR2021/014352 dated Jan. 24, 2022 (PCT/ISA/210).
Supplementary European Search Report dated Jan. 9, 2024 in Application No. 21 90 6813.

* cited by examiner

BREAD COMPRISING SACCHARIFIED RICE SOLUTION AND METHOD FOR PREPARING SAME

CROSS REFERENCE TO RELATED APPLICATIONS

This application is a National Stage of International Application No. PCT/KR2021/014352 filed Oct. 15, 2021, claiming priority based on Korean Patent Application No. 10-2020-0176742 filed Dec. 16, 2020.

TECHNICAL FIELD

The present invention relates to bread containing a saccharified rice solution and a method for preparing the same and more specifically, to bread containing a saccharified rice solution prepared using *Aspergillus oryzae* koji, *Aspergillus kawachii* koji and lees, and a method for preparing the same.

BACKGROUND ART

In general, bread refers to a product by fermenting a mixture of wheat flour as a main ingredient with water, and then baking the resulting product in an oven. Flour, salt, water, yeast, and dairy products are blended to prepare a dough. In this case, nuts or dried fruits are also added thereto. The quality of bread may depend on the ratio of ingredients and the preparation process. The fermentation process is very important in order to produce high-quality bread and greatly affects the physical properties and flavor of the bread.

Recently, research has been conducted on baking using saccharified rice. In the prior art, Korean Patent No. 10-1750154 discloses a rice fermented composition and rice bread having superior effect of aging-retardation and a method of preparing the same, and Korean Patent No. 10-1926741 entitled "natural fermented bread using rice" discloses a method of improving the quality of bread using fermented rice broth. Therefore, the present invention discloses a method of preparing a saccharified rice solution having improved taste and flavor while solving the problems of conventional saccharified rice solutions, and a method of producing bread containing the same.

DISCLOSURE

Technical Problem

Conventionally, a saccharified rice solution has been prepared using *Aspergillus oryzae* koji or *Aspergillus kawachii* koji. In this case, the sweetness increases depending on saccharification. However, there is a recent trend in which consumers are averse to sweet flavors. Therefore, the present invention aims at preparing a saccharified rice solution that has improved various and rich flavors including umami and reduced sweetness compared to a conventional saccharified rice solution prepared using *Aspergillus oryzae* koji or *Aspergillus kawachii* koji, and developing bread with improved various and rich flavors including umami, containing the saccharified rice solution.

Technical Solution

In accordance with one aspect of the present invention, the above and other objects can be accomplished by the provision of a saccharified rice solution prepared by adding *Aspergillus oryzae* koji, *Aspergillus kawachii* koji and lees to rice flour or rice, followed by hydrolysis.

Meanwhile, the rice flour is preferably alpha rice flour.

Meanwhile, the saccharified rice solution is preferably prepared by further adding glucose or rice syrup to the rice flour or rice, followed by hydrolysis.

In accordance with another aspect of the present invention, provided is a flour dough for baking containing the saccharified rice solution.

In accordance with another aspect of the present invention, provided is bread prepared by baking the dough.

Advantageous Effects

The present invention provides a saccharified rice solution that is prepared using *Aspergillus oryzae* koji, *Aspergillus kawachii* koji and lees, and thus is capable of reducing sweetness, providing a further enhanced umami taste based on increased contents of glutamic acid and aspartic acid, and improving various and rich flavors (aroma) compared to a conventional saccharified rice solution prepared using *Aspergillus oryzae* koji or *Aspergillus kawachii* koji.

BEST MODE

Figure 1:
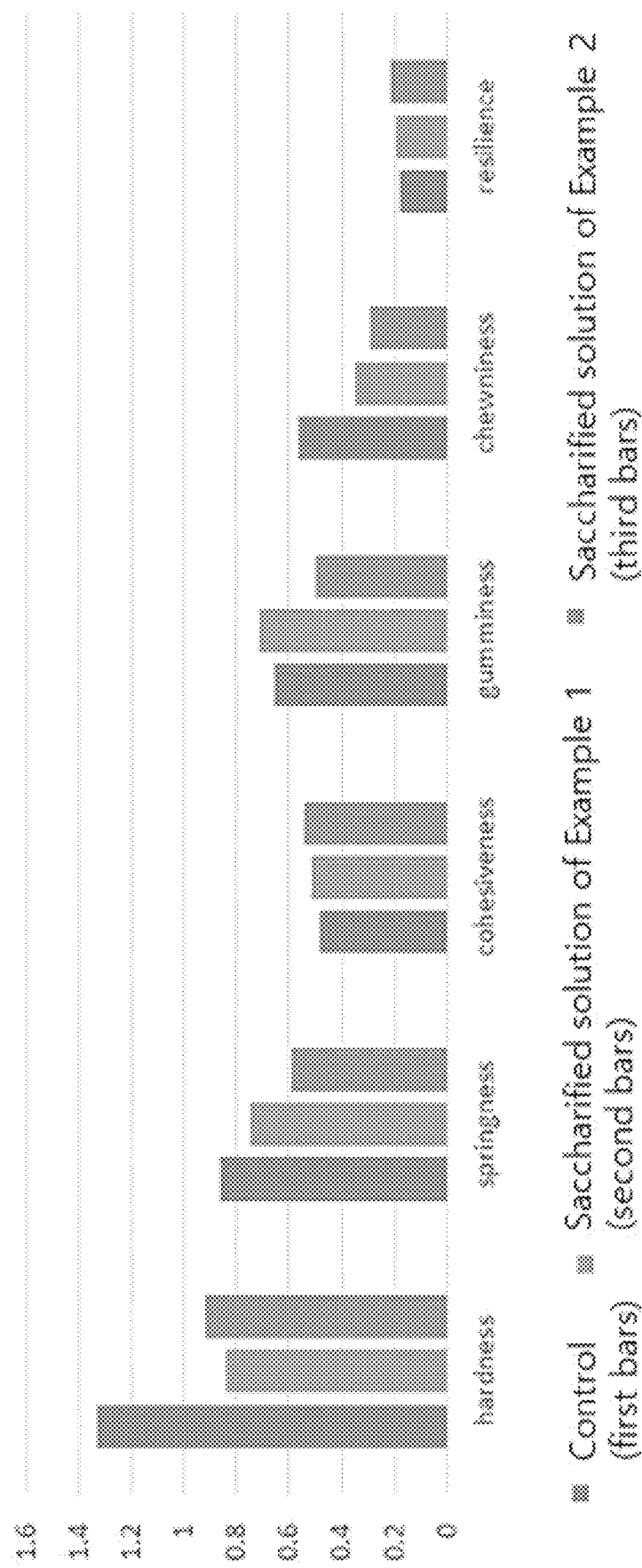
FIG. 1 is a graph showing the results of analysis of the physical properties of bread produced using the saccharified rice solution of the present invention.

Conventionally, a saccharified rice solution has been prepared using *Aspergillus oryzae* koji or *Aspergillus kawachii* koji. In this case, the sweetness increases due to saccharification. However, there is a recent trend in which consumers are averse to sweet flavors. Therefore, the present inventors made extensive efforts to develop a saccharified rice solution that reduces sweetness and improves various and rich flavors including umami, while maintaining the advantages of conventional saccharified rice solutions prepared using *Aspergillus oryzae* koji or *Aspergillus kawachii* koji.

The present invention provides a saccharified rice solution prepared by hydrolyzing rice flour or rice to which *Aspergillus oryzae* koji, *Aspergillus kawachii* koji and lees have been added.

In the present invention, an optimum process of preparing a saccharified rice solution having a high sensory score was established by mixing *Aspergillus oryzae* koji with *Aspergillus kawachii* koji at an optimum ratio of 2.5 to 3.5:6.5 to 7.5, further adding lees thereto and performing efficient starch pre-treatment and sugar supplementation (treatment with glucose and rice syrup). At this time, more preferably, *Aspergillus oryzae* koji is mixed with *Aspergillus kawachii* koji at a ratio of 3:7. As described above, the saccharified rice solution prepared using *Aspergillus oryzae* koji, *Aspergillus kawachii* koji and lees is capable of reducing sweetness to an appropriate level and improving various and rich flavors (fragrance) including umami compared to a saccharified rice solution prepared using only *Aspergillus oryzae* koji, or *Aspergillus kawachii* koji.

In addition, the contents of aspartic acid and glutamic acid showing the umami in the saccharified solution containing only *Aspergillus oryzae* koji or *Aspergillus kawachii* koji are 0.016% and 0.033%, respectively, but the contents of aspartic acid and glutamic acid in the saccharified solution containing *Aspergillus oryzae* koji, *Aspergillus kawachii* koji and lees are 0.023% and 0.049%, which correspond to 69.5% and 67.3% increases, respectively. As described above, the saccharified rice solution prepared using *Aspergillus oryzae* koji, *Aspergillus kawachii* koji and lees according to the present invention exhibits remarkably improved umami compared to a saccharified rice solution prepared using only *Aspergillus oryzae* koji, or *Aspergillus kawachii* koji.

Meanwhile, any rice flour may be used as the rice flour without limitation as long as it is known in the art, but the rice flour is preferably alpha rice flour. The alpha rice flour means alpha ($\alpha$)-starch rice flour (i.e., rice flour gelatinized into alpha-starch).

Meanwhile, in the present invention, the saccharified rice liquid is preferably prepared by hydrolyzing rice flour or rice to which glucose or rice syrup has been further added.

The *Aspergillus oryzae* koji derived from *Aspergillus oryzae* and the *Aspergillus kawachii* koji derived from *Aspergillus kawachii* were used.

The term "lees" refers to the residue left behind after the liquor ingredient is filtered from raw rice wine or sake (unfiltered liquor), which is also called "sake lees". Lees contain large amounts of dietary fibers, proteins, amino acids, organic acids and vitamins, as well as enzymes such as amylase and protease. Here, saccharification of *Rhizopus oryzae* left over lees was used.

Meanwhile, the present invention provides a flour dough for baking containing the saccharified rice solution.

Meanwhile, the flour dough for baking is preferably obtained by performing primary fermentation using strong flour, water, and yeast *Saccharomyces cerevisiae* SPC-SNU 70-1 (KCTC 12776BP) to prepare a sponge dough, adding the saccharified rice solution of the present invention to the sponge dough and then performing secondary fermentation on the resulting mixture.

Meanwhile, in the present invention, the sponge dough may be prepared under any fermentation conditions that allow yeast strains to grow. Preferably, the dough is mixed at a temperature of 24 to 26° C., is allowed to stand at 22 to 28° C. for 20 to 40 minutes, and is fermented at a low temperature of 4 to 8° C. for 14 to 18 hours. The fermentation at a low temperature for a long time as in the above conditions has advantages of causing accumulation of metabolites and increasing extensibility and flavors of the product. In addition, such a method has a low production risk and high efficiency compared to a straight method.

Meanwhile, in the process of preparing the dough of the present invention, the fermentation is preferably performed such that the dough is mixed at a temperature of 26 to 28° C., intermediate fermentation is performed at a temperature of 25 to 28° C. and a relative humidity of 80 to 90% for 20 to 40 minutes, rounding is performed and aging is performed at a temperature of 25 to 28° C. and a relative humidity of 80 to 90% for 10 to 20 minutes. Through the above process, gluten is rearranged and stabilized to prepare for fermentation.

Also, the present invention provides bread prepared by baking the dough.

Also, the present invention provides bread prepared by baking the dough.

Any dough may be used as the dough for baking as long as it is generally prepared by adding water and the like to wheat flour, and if necessary, by adding salt (preferably refined salt), refined sugar, shortening, or the like thereto.

The term "baking" used herein generally means a process of baking to produce bread, and specifically refers to a method of baking using dry heat in an oven. Since a known conventional method can be used, a detailed description thereof will be omitted.

As can be seen from the following example, the present invention provides a saccharified rice solution that is prepared using an *Aspergillus oryzae* koji, an *Aspergillus kawachii* koji, and lees and thus is capable of reducing sweetness and improving various and rich flavors (fragrance) including umami taste, compared to a conventional saccharified rice solution prepared using *Aspergillus oryzae* koji or *Aspergillus kawachii* koji. Also, bread having excellent various and rich flavors (fragrance) including umami taste can be produced using the saccharified rice solution.

Hereinafter, the present invention will be described in more detail with reference to the following examples. The scope of the present invention is not limited to the examples, and encompasses modifications of the technical concept equivalent thereto.

Example 1: Preparation of Saccharified Rice Solution Using *Aspergillus oryzae* Koji and *Aspergillus kawachii* Koji of Present Invention In this example, an optimal process for preparing a saccharified rice solution having excellent sensory scores was established by setting an optimal mixing ratio of *Aspergillus oryzae* koji to *Aspergillus kawachii* koji and then further performing efficient starch pre-treatment and sugar supplementation (treatment with glucose and rice syrup).

1) Analysis Method

For analysis of the saccharified rice solution, pH, TTA (measurement of acidity), Brix (measurement of sweetness), organic acid, free sugar, and free amino acid were analyzed and sensory evaluation was performed.

Specifically, pH analysis was performed by homogenizing a mixture of 5 g of a sample with 95 mL of distilled water and then measuring the pH of the resulting sample three times using a pH meter. For TTA analysis, the appropriate amount of NaOH was measured in accordance with 6.8.1.1 Acidity, 6. the Food Standards Test Method, 8. General Test Method, in Food Codex. For Brix analysis, the refractive index of the saccharometer was measured in accordance with 2.1.4.1 saccharide, 2. Food Ingredients Test Method, 8. General Test Method in Food Codex. For sensory evaluation, properties, taste, texture, and color were evaluated in accordance with 1.1 Property (sensory evaluation), 1. Food General Test Method, 8. General Test Method in Food Codex.

In addition, the organic acids, free sugars, and free amino acids were assayed by instrumental analysis, and detailed analysis conditions are shown in Tables 1 to 3.

TABLE 1

| Organic acid assay | |
| --- | --- |
| Analytical Instrument | UPLC (Waters, USA) Model name: Acquity UPLC |
| Column | Unison US-C18 (Imtakt, USA) 250 × 4.6 mm, 5 μm |
| Detector | PDA (Waters, USA) |
| Analysis conditions | Mobile Phase: 0.1% phosphoric acid<br>Flow rate: 0.7 ml/min<br>Column Temperature: 25° C.<br>Sample Temperature: 20° C. |

TABLE 1-continued

Organic acid assay

| | |
|---|---|
| Sample preparation | 2 g of sample is diluted 10x with tertiary DW (w/w %), followed by mixing under vortexing.<br>After centrifugation, the supernatant is diluted at a suitable ratio for analysis (final dilution ratio of 1/20), and then filtered through 0.45 μm filter.<br>Instrumental analysis |

TABLE 2

Free sugar analysis

| | |
|---|---|
| Analytical Instrument | HPLC (Shiseido, USA) Model name: Nanospace S1-2 |
| Column | Carbohydrate High Performance (Waters) 4.6 × 450 mm, 4 μm |
| Detector | RID (Shiseido, USA) |
| Analysis conditions | Mobile Phase: 80% Acetonitrile<br>Flow rate: 1 ml/min<br>Column Temperature: 35° C. |
| Sample preparation | 2 g of sample is diluted 10x with tertiary DW (w/w %), followed by mixing (under vortexing, product (bread): Sonication 5 min)<br>After centrifugation, the supernatant is diluted at a suitable ratio for analysis and then filtered through 0.45 μm filter. (final dilution ratio: material 1/100, product (bread) 1/10)<br>Instrumental analysis |

TABLE 3

Free amino acid assay

| | |
|---|---|
| Analytical Instrument | HPLC (Thremo Dionex, USA) Model name: Dionex Ultimate 3000 |
| Column | Inno C18 column (YoungJin Biochrom, Korea) 4.6 × 450 mm, 5 μm |
| Detector | FL Detector (Agilent, USA) |
| Analysis conditions | Mobile Phase A: 40 mM Sodium phosphate, pH 7<br>Mobile Phase B: 3DW/Acetonitrile/Methanol (10:45:45 v/v %)<br>Flow rate: 1.5 ml/min<br>Column Temperature: 40° C.<br>Sample Temperature: 20° C. |

TABLE 3-continued

Free amino acid assay

| | |
|---|---|
| Sample preparation | 2 g of sample is diluted 10x with tertiary DW (w/w %), followed by mixing under vortexing.<br>After centrifugation, the supernatant is diluted at a suitable ratio for analysis and then filtered through 0.45 μm filter.<br>Instrumental analysis |

2) Setting Optimal Mixing Ratio of Saccharified Rice Solution Using *Aspergillus oryzae* Koji and *Aspergillus kawachii* Koji In the present invention, a saccharified rice solution exhibiting excellent sensory properties was prepared using *Aspergillus oryzae* koji and *Aspergillus kawachii* koji, instead of malt, which is generally used as an enzyme source. During the saccharification process, *Aspergillus oryzae* formed in *Aspergillus oryzae* koji, produces saccharides, decomposes rice proteins to produce amino acids, and creates a mild sweetness. In addition, *Aspergillus kawachii* formed in *Aspergillus kawachii* koji produces various organic acids, especially fresh acidic flavor (citric acid). Based thereon, *Aspergillus kawachii* can create a variety of tastes (sour taste and umami taste) than conventional saccharified liquids (e.g., Sikhye (Korean traditional rice beverage).

Meanwhile, in the present invention, it was attempted to set the optimal mixing ratio of *Aspergillus oryzae* koji to *Aspergillus kawachii* koji. For this purpose, saccharified rice solutions were prepared by varying the mixing ratio of *Aspergillus oryzae* koji to *Aspergillus kawachii* koji, the pH, TTA, Brix, total organic acid content, total free sugar content, and total free amino acid content of the saccharified rice solutions were measured and sensory evaluation was performed. The results are shown in Table 4. In addition, the results for detailed components of metabolites, organic acids, free sugars, and free amino acids are shown in Table 5. Based thereon, it was possible to calculate the optimal mixing ratio (2.5-3.5:6.5-7.5) of *Aspergillus oryzae* koji to *Aspergillus kawachii* koji, which had the best sensory score.

TABLE 4

| | T1 | T2 | T3 | T4 | T5 |
|---|---|---|---|---|---|
| Hard rice | 21.74 | 21.74 | 21.74 | 21.74 | 21.74 |
| *Aspergillus oryzae* koji | 10.87 | 15.22 | 21.74 | 0 | 6.52 |
| *Aspergillus kawachii* koji | 10.87 | 6.52 | 0 | 21.74 | 15.22 |
| Feed water | 56.52 | 56.52 | 56.52 | 56.52 | 56.52 |
| Total | 100 | 100 | 100 | 100 | 100 |
| Remarks | *Aspergillus oryzae* koji:*Aspergillus kawachii* koji = 5:5 | *Aspergillus oryzae* koji:*Aspergillus kawachii* koji = 7:3 | *Aspergillus oryzae* koji 100% | *Aspergillus kawachii* koji 100% | *Aspergillus oryzae* koji:*Aspergillus kawachii* koji = 3:7 |
| Brix (Sweetness measurement) | 43.3 | 43.4 | 45.3 | 42.8 | 42.1 |
| pH | 4.47 | 4.79 | 5.94 | 3.92 | 4.18 |
| TTA (Acidity measurement) | 5.98/12.29 | 4.03/10.02 | 1.07/5.73 | 12.14/19.38 | 8.35/14.82 |
| Total organic acid (%) | 0.217 | 0.156 | 0.033 | 0.300 | 0.273 |

TABLE 4-continued

|  | T1 | T2 | T3 | T4 | T5 |
|---|---|---|---|---|---|
| Total free sugar (%) | 30.328 | 30.244 | 32.482 | 28.795 | 26.891 |
| Total free amino acid (%) | 0.378 | 0.414 | 0.395 | 0.338 | 0.371 |
| Sensory score (9-point scale) | 5.84 | 5.59 | 3.41 | 4.52 | 7.21 |

TABLE 5

| | Analysis items | T1 | T2 | T3 | T4 | T5 |
|---|---|---|---|---|---|---|
| Organic acid (%) | Malic acid | 0.063 | 0.058 | 0.024 | 0.041 | 0.021 |
| | Lactic acid | 0.021 | 0.006 | 0.000 | 0.099 | 0.067 |
| | Acetic acid | 0.000 | 0.000 | 0.000 | 0.000 | 0.000 |
| | Citric acid | 0.000 | 0.000 | 0.000 | 0.000 | 0.000 |
| | Succinic acid | 0.124 | 0.084 | 0.000 | 0.152 | 0.186 |
| | Fumaric acid | 0.009 | 0.009 | 0.009 | 0.008 | 0.000 |
| | Total | 0.217 | 0.156 | 0.033 | 0.300 | 0.273 |
| Free sugar (%) | Fructose | 0.000 | 0.000 | 0.000 | 0.000 | 0.000 |
| | Glucose | 23.369 | 25.381 | 27.353 | 23.951 | 22.528 |
| | Sucrose | 0.000 | 0.000 | 0.000 | 0.000 | 0.000 |
| | Maltose | 6.959 | 4.862 | 5.129 | 4.844 | 4.363 |
| | Lactose | 0.000 | 0.000 | 0.000 | 0.000 | 0.000 |
| | Total | 30.328 | 30.244 | 32.482 | 28.795 | 26.891 |
| Free amino acid (%) | Aspartic acid | 0.017 | 0.019 | 0.027 | 0.014 | 0.016 |
| | Glutamic acid | 0.036 | 0.041 | 0.047 | 0.028 | 0.033 |
| | Asparagine | 0.019 | 0.019 | 0.014 | 0.015 | 0.017 |
| | Serine | 0.015 | 0.018 | 0.025 | 0.009 | 0.013 |
| | Glutamine | 0.028 | 0.033 | 0.028 | 0.016 | 0.022 |
| | Histidine | 0.011 | 0.010 | 0.007 | 0.009 | 0.010 |
| | Glycine | 0.009 | 0.011 | 0.015 | 0.005 | 0.007 |
| | Threonine | 0.011 | 0.015 | 0.019 | 0.006 | 0.009 |
| | Arginine | 0.002 | 0.001 | 0.001 | 0.062 | 0.038 |
| | Alanine | 0.024 | 0.028 | 0.032 | 0.017 | 0.021 |
| | GABA | 0.002 | 0.003 | 0.005 | 0.002 | 0.002 |
| | Tyrosine | 0.028 | 0.030 | 0.024 | 0.024 | 0.026 |
| | Valine | 0.022 | 0.026 | 0.027 | 0.011 | 0.018 |
| | Methionine | 0.011 | 0.012 | 0.011 | 0.009 | 0.010 |
| | Ornithine | 0.000 | 0.000 | 0.000 | 0.000 | 0.000 |
| | Tryptophan | 0.008 | 0.009 | 0.008 | 0.008 | 0.009 |
| | Phenylalanine | 0.030 | 0.032 | 0.016 | 0.026 | 0.028 |
| | Isoleucine | 0.015 | 0.019 | 0.020 | 0.007 | 0.011 |
| | Leucine | 0.048 | 0.050 | 0.039 | 0.041 | 0.045 |
| | Lysine | 0.025 | 0.023 | 0.014 | 0.020 | 0.024 |
| | Proline | 0.017 | 0.016 | 0.017 | 0.019 | 0.014 |
| | Total | 0.378 | 0.414 | 0.395 | 0.338 | 0.371 |

3) Preparation of Saccharified Rice Solution at Optimum Mixing Ratio of *Aspergillus oryzae* Koji to *Aspergillus kawachii* Koji Using Addition of Sugar Supplementation The sugar content in the saccharified rice solution prepared at the optimal mixing ratio of *Aspergillus oryzae* koji to *Aspergillus kawachii* koji (2.5~3.5:6.5~7.5) was corrected and sugar supplementation was performed to prevent quality deviation. In order to confirm the optimal sugar supplementation, pH, TTA, Brix and total free sugar content of the saccharified rice solution prepared by changing the mixing ratio of supplemented sugar components (glucose, sugar, rice syrup) were measured and sensory evaluation was performed. The results were as shown in Table 6, which shows that the experimental group supplemented with glucose and rice syrup had the best sensory score as the harmony of sweetness was the best.

TABLE 6

|  | T6 | T7 | T8 | T9 | T10 | T11 |
|---|---|---|---|---|---|---|
| Hard rice | 21.74 | 21.74 | 21.74 | 21.74 | 21.74 | 21.74 |
| *Aspergillus oryzae* koji | 6.52 | 6.52 | 6.52 | 6.52 | 6.52 | 6.52 |
| *Aspergillus kawachii* koji | 15.22 | 15.22 | 15.22 | 15.22 | 15.22 | 15.22 |
| Feed water | 56.52 | 56.52 | 56.52 | 56.52 | 56.52 | 56.52 |
| Total | 100 | 100 | 100 | 100 | 100 | 100 |
| Glucose | 25 | 0 | 0 | 12.5 | 0 | 12.5 |
| Rice syrup | 0 | 25 | 0 | 0 | 12.5 | 12.5 |
| Sugar | 0 | 0 | 25 | 12.5 | 12.5 | 0 |
| Remarks | Glucose | Rice syrup | Sugar | Glucose, sugar | Sugar, rice syrup | Glucose, rice syrup |
| Brix | 41.6 | 40.3 | 43.9 | 43.2 | 42.1 | 42.1 |
| pH | 4.04 | 4.07 | 4.02 | 4.04 | 4.01 | 4.18 |
| TTA (Acidity measurement) | 6.44/11.13 | 6.71/12.02 | 6.57/11.31 | 6.33/11.01 | 7.13/12.50 | 8.35/14.82 |
| Total free sugar (%) | 31.850 | 22.790 | 31.110 | 31.090 | 27.030 | 26.891 |
| Sensory score (9-point scale) | 5.25 | 5.09 | 5.46 | 6.84 | 6.45 | 7.14 |

4) Preparation of Saccharified Rice Solution Prepared at Optimum Mixing Ratio of *Aspergillus oryzae* Koji to *Aspergillus kawachii* Koji, while Performing Sugar Supplementation and Varying Starch Pre-Treatment Process A saccharified rice solution was prepared at the optimal mixing ratio of *Aspergillus oryzae* koji to *Aspergillus kawachii* koji (2.5~3.5:6.5~7.5), while performing sugar supplementation and changing starch pre-treatment (gelatinization, a-starch). The pH, TTA, Brix and total free sugar content of the saccharified rice solution were measured and sensory evaluation thereof was performed. The moisture content of hard rice prepared by the gelatinization process was calculated, the content of alpha rice flour (rice flour) prepared by the a-starch preparation process was reduced, and the feed water content was increased to adjust the content of the starch used for saccharification to a similar level thereto. The results of total organic acids, total free sugars, total free amino acids and sensory scores after starch pretreatment (gelatinization, a-starch) were overall similar (Table 7). Therefore, it is possible to use alpha rice flour (rice flour) instead of hard rice in the preparation process. Based thereon, it is possible to shorten the process of preparing hard rice and pulverize raw materials and thereby to improve shelf life and production workability.

TABLE 7

| | T12 | T13 |
|---|---|---|
| Hard rice | 21.74 | 0 |
| *Aspergillus oryzae* koji | 6.52 | 6.25 |
| *Aspergillus kawachii* koji | 15.22 | 14.58 |
| Feed water | 56.52 | 64.58 |
| Alpha rice flour (Rice flour) | 0 | 14.58 |
| Total | 100 | 100 |
| Glucose | 12.5 | 12.5 |
| Rice syrup | 12.5 | 12.5 |
| Total | 125 | 125 |
| Brix | 42.1 | 41.9 |
| pH | 4.18 | 4.31 |
| TTA (acidity measurement) | 8.35/14.82 | 8.16/14.97 |
| Total organic acid (%) | 0.273 | 0.316 |
| Total free sugar (%) | 26.891 | 25.881 |
| Total free amino acid (%) | 0.371 | 0.378 |
| Sensory score (9-point scale) | 7.21 | 7.29 |

Example 2: Preparation of Saccharified Rice Solution Using *Aspergillus oryzae* Koji, *Aspergillus kawachii* Koji and Lees of Present Invention In this example, a saccharified rice solution was prepared by adding lees in order to supplement the saccharified rice solution using *Aspergillus oryzae* koji or *Aspergillus kawachii* koji in Example 1. In the saccharification process of *Rhizopus oryzae* remaining in lees, starch is decomposed to produce free sugars and amino acids.

The pH, TTA, Brix, total organic acid content, total free sugar content, and total free amino acid content of the saccharified rice solution prepared by varying the amount of lees while *Aspergillus oryzae* koji and *Aspergillus kawachii* koji are used at the optimal mixing ratio were measured and sensory evaluation was performed. The results are shown in Table 8. In particular, as the alpha rice flour content of the starch material increases, the metabolite content and the sensory evaluation score increase. Therefore, among the saccharified rice solutions to which lees were added, T15 was set as the optimal experimental group.

TABLE 8

| | T14 | T15 | T16 | T17 |
|---|---|---|---|---|
| *Aspergillus oryzae* koji | 2.65 | 2.29 | 2.65 | 2.39 |
| *Aspergillus kawachii* koji | 6.35 | 5.72 | 6.35 | 5.74 |
| Feed water | 31.75 | 29.85 | 42.33 | 33.49 |
| Lees | 52.91 | 45.72 | 42.33 | 52.63 |
| Alpha rice flour (rice flour) | 6.35 | 16.43 | 6.35 | 5.74 |
| Total | 100 | 100 | 100 | 100 |
| Glucose | 5.3 | 5.1 | 5.3 | 5.3 |
| Rice syrup | 5.3 | 5.1 | 5.3 | 5.3 |
| Total | 110.58 | 110.58 | 110.58 | 110.58 |
| Brix (Sweetness measurement) | 27.7 | 34.9 | 26.7 | 27 |
| pH | 4.42 | 4.27 | 4.16 | 4.14 |
| TTA (Acidity measurement) | 7.46/13.40 | 9.11/14.10 | 7.34/13.10 | 8.33/13.86 |
| Total organic acid (%) | 0.3231 | 0.218 | 0.280 | 0.309 |
| Total free sugar (%) | 14.859 | 16.390 | 15.641 | 13.797 |
| Total free amino acid (%) | 0.394 | 0.379 | 0.399 | 0.391 |
| Sensory score (9-point scale) | 4.86 | 6.72 | 5.18 | 5.54 |
| Remarks | Low alpha rice flour content | | Low lees content | High lees content |

Meanwhile, in order to perform sensory evaluation upon addition of lees, the contents of ingredients of free amino acids were further analyzed. As a result, as shown in Table 9, the contents of glutamic acid and aspartic acid, which are amino acids related to umami, in T15 (saccharified rice solution containing lees, Table 8) compared to T5 (saccharified rice solution without lees, Table 4) were high, and the contents of proline, ornithine, and leucine, which were used to create a strong flavor felt in the bread crust, were high. This indicates that the umami taste and flavor are enhanced by the addition of lees.

TABLE 9

| Analysis items | | T5 | T15 |
|---|---|---|---|
| Free amino acid (%) | Aspartic acid | 0.016 | 0.023 |
| | Glutamic acid | 0.033 | 0.049 |
| | Asparagine | 0.017 | 0.023 |
| | Serine | 0.013 | 0.019 |
| | Glutamine | 0.022 | 0.027 |
| | Histidine | 0.010 | 0.014 |
| | Glycine | 0.007 | 0.018 |
| | Threonine | 0.009 | 0.014 |
| | Arginine | 0.038 | 0.073 |
| | Alanine | 0.021 | 0.042 |
| | GABA | 0.002 | 0.003 |
| | Tyrosine | 0.026 | 0.030 |
| | Valine | 0.018 | 0.021 |
| | Methionine | 0.010 | 0.011 |
| | Ornithine | 0.000 | 0.006 |

TABLE 9-continued

| Analysis items | T5 | T15 |
| --- | --- | --- |
| Tryptophan | 0.009 | 0.027 |
| Phenylalanine | 0.028 | 0.011 |
| Isoleucine | 0.011 | 0.000 |
| Leucine | 0.045 | 0.042 |
| Lysine | 0.024 | 0.036 |
| Proline | 0.014 | 0.032 |
| Total | 0.371 | 0.52 |

Overall, by addition of lees, it was possible to prepare a saccharified rice solution with enhanced various rich flavor, including umami, while appropriately reducing the sweetness created in the saccharified rice solution using *Aspergillus oryzae* koji or *Aspergillus kawachii* koji.

Example 3: Preparation of Bread Using Saccharified Rice Solutions of Examples 1 and 2 and Testing In this example, bread (plain bread) was prepared using the saccharified rice solutions of Example 1 (containing *Aspergillus oryzae* koji and *Aspergillus kawachii* koji) and Example 2 (containing *Aspergillus oryzae* koji, *Aspergillus kawachii* koji and lees) and tested.

1) Preparation of Bread (Plain Bread) Using Saccharified Rice Solutions of Examples 1 and 2

The components of the sponge dough (see Table 10 below) were put into a mixer (product name: SK101S MIXER: Japan), kneaded in the second stage for 2 minutes and in the third stage for 1 minute, and mixed such that the final temperature of the dough was 25° C. Then, the dough was allowed to stand at room temperature for 30 minutes, and then primarily fermented in a fermenter at 6° C. for 16 hours to prepare sponge dough. Then, the components of the dough (see Table 10 below) are put into a mixer (product name: SK101S MIXER: Japan), kneaded in the first stage for 1 minute, the sponge dough was added thereto, and the resulting mixture was kneaded in the second stage for 3 minutes and in the third stage for 3 minutes, and mixed such that the final temperature of the dough was 27° C. The dough was intermediate-fermented in a fermenter at 27° C. and a relative humidity of 85% for 30 minutes, was divided into uniform segments, rounded, and aged in a fermenter at 27° C. and a relative humidity of 85% for 15 minutes. After aging, the dough was molded and placed in a bread case. Then, the dough placed in the bread case was fermented at 37° C. and at a relative humidity of 85% for 50 minutes to prepare bread dough. The prepared bread dough was baked in an oven at an upper heat of 170° C. and at a lower heat of 210° C. for 35 minutes, and then was cooled at room temperature until the internal temperature reached 32° C.

TABLE 10

| | | Control group | Addition of Example 1 saccharified rice solution | Addition of Example 2 saccharified rice solution |
| --- | --- | --- | --- | --- |
| Sponge dough | Strong flour | 70 | 70 | 70 |
| | Commercial yeast: *Saccharomyces cerevisiae* (SPC-SNU 70-1 (KCTC 12776BP)[a] | 0.7 | 0.7 | 0.7 |
| | Rimusoft[b] | 0.3 | 0.3 | 0.3 |
| | Feed water | 42 | 42 | 42 |
| Dough | Strong flour | 3 | 30 | 30 |
| | Refined salt | 1.8 | 1.8 | 1.8 |
| | White sugar | 7 | 7 | 7 |
| | Whole milk powder | 3 | 3 | 3 |
| | Butter | 10 | 10 | 10 |
| | Commercial yeast | 0.6 | 0.6 | 0.6 |
| | Feed water | 13 | 7 | 8 |
| | Example 1 saccharified rice solution (T13) | 0 | 10 | 0 |
| | Example 2 saccharified rice solution (T15) | 0 | 0 | 10 | a: *Saccharomyces cerevisiae* SPC-SNU 70-1 (KCTC 12776BP) is derived from Korean Patent No. 10-1551839 (Registration date: Sep. 3, 2015) b: Rimusoft is an emulsifier as a food additive (glycerin fatty acid ester) and represents "Rimusoft super (v)".

2) Texture and Ingredient Analysis and Sensory Evaluation of Bread

The texture and component analysis, and sensory evaluation of bread prepared using the saccharified rice solutions of Examples 1 and 2 above were performed.

First, the texture (physical property) was compared using a texture analyzer (Stable Micro Systems texture analyzer). As analysis indicators, hardness, cohesiveness, springiness, gumminess, chewiness, and resilience were measured. A higher hardness value indicates higher hardness. Springiness means the degree to which a substance returns to its original state, cohesiveness means the ability of food to retain its original state, gumminess means stickiness, chewiness refers to the degree of swallowing, and resilience refers to a force at which an object is restored after pressed. Each analysis parameter was repeatedly measured in 3 replicates.

As a result, as can be seen from FIG. 1 and Table 11, both bread produced using the saccharified solutions of Examples 1 and 2 had improved overall texture (decreased hardness, increased cohesiveness and resilience, and maintained springiness).

TABLE 11

|  | Hardness | Springiness | Cohesiveness | Gumminess | Chewiness | Resilience |
|---|---|---|---|---|---|---|
| Control group | 1.336 | 0.863 | 0.489 | 0.654 | 0.564 | 0.181 |
| Example 1 saccharified rice solution | 0.84 | 0.746 | 0.513 | 0.712 | 0.349 | 0.194 |
| Example 2 saccharified rice solution | 0.92 | 0.592 | 0.542 | 0.498 | 0.295 | 0.213 |

Then, the free sugar component was analyzed (see Table 2), and the fragrance component was compared using the GS/MS system (Table 12).

TABLE 12

| Analysis system | Operation conditions |
|---|---|
| GC/MS analysis | *GC Model name: Agilent 7890A<br>*Inlet temperature: 230° C.<br>*Column: DB-WAX (60 m × 250 um × 0.25 uM)<br>*Carrier gas: helium<br>*Flow rate: 1 ml/min<br>*Oven temperature program : from 40° C. (5 min) → 8° C./min → 230° C. (10 min)<br>*MS detector: Agilent 5975C MSD (EI mode) |
| SPME analysis | * Fiber: DVB/Carboxen/SPME (Supelco Co.)<br>* Sample equilibration time<br>incubation temp. 85° C.<br>incubation time 30 min |

As a result, as can be seen from Table 13, the bread made using the saccharified solution of Example 2 exhibited an increase in various types of sweetness (increased content of several free sugars) compared to the control group, and exhibited an appropriately reduced sweetness compared to bread made using the saccharified solution of Example 1. That is, the bread made using the saccharified solution of Example 2 had an appropriate sweetness.

TABLE 13

| Free sugar (%) | Control | Example 1 saccharified rice solution | Example 2 saccharified rice solution |
|---|---|---|---|
| Fructose | 0.75 | 1.22 | 1.10 |
| Glucose | 0.46 | 2.26 | 1.14 |
| Sucrose | 0.00 | 0.00 | 0.00 |
| Maltose | 2.10 | 2.04 | 1.83 |
| Lactose | 0.82 | 0.89 | 0.94 |
| Total | 4.13 | 6.42 | 5.01 |

Meanwhile, sensory evaluation was performed on the saccharified rice solutions of Examples 1 and 2. As a result, as can be seen from Table 14, the sensory score was higher in bread made using the saccharified solutions of Examples 1 and 2 compared to the control group, and in particular, the saccharified rice solution of Example 2 exhibited an improved umami taste compared to the saccharified rice solution of Example 1. This indicates that the umami taste and flavor are enhanced by the addition of lees.

TABLE 14

| Analysis items | | Control | Saccharified rice solution of Example 1 | Saccharified rice solution of Example 2 |
|---|---|---|---|---|
| Sensory evaluation (9-point scale) | Sweetness | 4.85 | 8.26 | 6.45 |
| | Saltiness | 5.16 | 5.03 | 5.71 |
| | Sourness | 4.96 | 5.24 | 5.69 |
| | Umami | 5.48 | 6.33 | 8.17 |
| | Overall | 5.11 | 7.21 | 7.94 |

Figure 2:
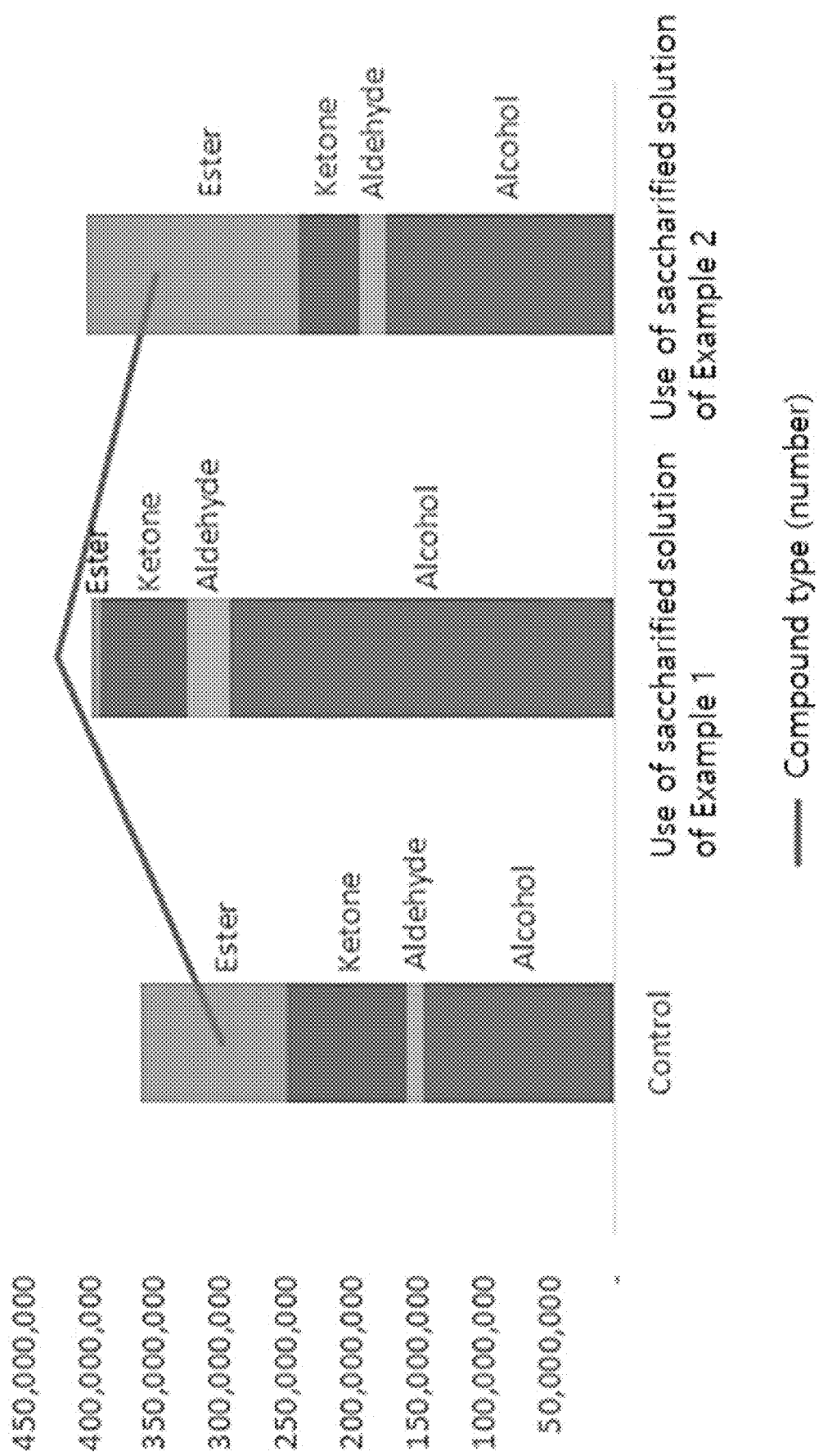
FIG. 2 is a graph showing the results of analysis of aroma components of bread produced using the saccharified rice solution of the present invention.

Meanwhile, as shown in FIG. 2 and Table 15, the bread prepared using the saccharified solutions of Examples 1 and 2 were detected to have a greater variety of flavor ingredients (Example 1: 17 types, Example 2: 14 types) than the control group (12 types). Bread prepared using the saccharified rice solution of Example 1 was found to have a great amount of alcohol having fruity, floral, and whiskey flavors, and a great amount of aldehyde having savory flavors such as roasted, bread, and almond flavors. Bread made using the saccharified rice solution of Example 2 was found to have great amounts of alcohol having fruity, floral, and whiskey flavor characteristics, aldehyde having savory flavors such as roasted, bread, and almond flavors, and ester having sweet and fresh flavors such as fruity and apple flavors. This is considered to be due to various metabolites produced during the preparation of the saccharified rice solution of Example 2.

TABLE 15

| Flavor Area | | Control group | Saccharified rice solution of Example 1 | Saccharified rice solution of Example 2 | Description |
|---|---|---|---|---|---|
| Alcohol | Ethanol | 38,496,132 | 91,670,582 | 160,923,927 | Strong, Alcohol, Ethereal |
| | Isobutyl alcohol | 6,379,861 | 6,427,139 | 9,415,984 | Wine, malty |
| | 3-Methyl-1-butanol | — | 122,146,206 | — | Whiskey fruity banana |
| | 2-Heptanol | 1,469,788 | — | — | Fresh lemongrass herbal floral fruity |

TABLE 15-continued

| | Flavor Area | Control group | Saccharified rice solution of Example 1 | Saccharified rice solution of Example 2 | Description |
|---|---|---|---|---|---|
| | 1-Hexanol | — | — | 4,042,512 | Green, Fruity, Sweet, Woody, Floral |
| | Phenethyl alcohol | — | 73,224,730 | — | Rose-honey-like |
| Aldehyde | Total | 46,345,781 | 293,468,657 | 174,382,423 | |
| | 3-Methylbutane | — | 1,674,724 | — | Chocolate, Roasted Bread, Fruity, Corn flakes |
| | Hexanal | 2,813,624 | 2,146,948 | 2,120,518 | Fresh, Green, Fruity, Sweaty |
| | 2-Amylfuran | 2,631,942 | 2,355,922 | 2,251,848 | Fruity, Green, Earthy |
| | Acetoin | 2,934,085 | 4,467,510 | 3,029,328 | Sweet buttery creamy dairy milky fatty |
| | Nonanal | 3,296,232 | 1,681,528 | 2,714,667 | Waxy, green, fatty |
| | Furfural | — | 3,909,770 | — | Sweet, Almond, Bread |
| | Benzaldehyde | — | 12,784,843 | 10,714,977 | Almond, Strong, Bitter, Cherry |
| | Benzeneacetaldehyde | — | 3,012,631 | — | Honey, floral |
| Ketone | Total | 1,675,883 | 32,033,876 | 20,831,338 | |
| | 2-Heptanone | 32,696,033 | 22,106,778 | 15,733,276 | Fruity, Spicy, Sweet, Grass, Coconut, cinnamon |
| | 2-Nonanone | 59,845,480 | 32,634,616 | 29,141,357 | Fruity fresh sweet green weedy earthy herbal |
| | 2-Undecanone | — | 11,149,345 | 8,590,500 | Floral and fatty pineapple |
| Ester | Total | 92,541,513 | 65,890,739 | 53,465,133 | |
| | Isoamyl formate | 93,602,735 | — | 146,191,846 | Fruity green apple |
| | Ethyl hexanoate | 1,516,859 | — | 2,071,142 | Sweet, Fruity, Green, Creamy, Milky, Balsamic |
| | Hexyl formate | — | 2,531,475 | — | Green waxy floral herbal plum apple cucumber |
| | Ethyl octanoate | 14,551,853 | 4,392,463 | — | Fruity, Wine, Pear brandy, Banana, Sweet, Fresh |

TABLE 15-continued

| Flavor Area | Control group | Saccharified rice solution of Example 1 | Saccharified rice solution of Example 2 | Description |
|---|---|---|---|---|
| Diethyl succinate | — | — | 5,521,844 | Fruity apple, cooked apple, ylang-ylang |
| Total | 109,671,447 | 6,923,938 | 153,784,832 | |
| Total | 360,234,624 | 398,317,210 | 402,463,726 | |

Overall, it can be seen from the above results that, using the saccharified rice solution (Example 2) containing *Aspergillus oryzae* koji, *Aspergillus kawachii* koji and lees, it is possible to prepare a saccharified rice solution that is capable of reducing sweetness and improving various and rich flavors including umami due to the high contents of glutamic acid and aspartic acid, which are umami taste-related amino acids, compared to the saccharified rice solution containing *Aspergillus oryzae* koji and *Aspergillus kawachii* (Example 1).

The invention claimed is:

1. A method of preparing a saccharified rice solution comprising adding *Aspergillus oryzae* koji, *Aspergillus kawachii* koji and lees to a rice flour or rice, and conducting hydrolysis,
    wherein the *Aspergillus oryzae* koji and the *Aspergillus kawachii* koji are in a weight ratio of 2.5-3.5:6.5-7.5.

2. The method according to claim 1, wherein the rice flour is alpha rice flour.

3. The method according to claim 1, wherein the saccharified rice solution is prepared by further adding a glucose or rice syrup to the rice flour or rice prior to conducting hydrolysis.

4. A saccharified rice solution prepared by the method of claim 1,
    wherein the *Aspergillus oryzae* koji and the *Aspergillus kawachii* koji in the saccharified rice solution are in a weight ratio of 2.5-3.5:6.5-7.5.

5. A flour dough for baking comprising the saccharified rice solution according to claim 4.

6. A bread prepared by baking the flour dough according to claim 5.

* * * * *